US008058005B2

(12) United States Patent
Sun et al.

(10) Patent No.: US 8,058,005 B2
(45) Date of Patent: Nov. 15, 2011

(54) METHOD FOR SINGLE NUCLEOTIDE POLYMORPHISM AND MUTATION DETECTION USING REAL TIME POLYMERASE CHAIN REACTION MICROARRAY

(75) Inventors: Zhen Hong Sun, Shanghai (CN); Tao Pan, Shanghai (CN); Wendy Wang, Shanghai (CN); Hang Liao, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 364 days.

(21) Appl. No.: 12/256,979

(22) Filed: Oct. 23, 2008

(65) Prior Publication Data

US 2010/0105033 A1    Apr. 29, 2010

(51) Int. Cl.
*C12Q 1/68* (2006.01)
(52) U.S. Cl. .................................................. 435/6.11
(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 6,169,194 B1 * | 1/2001 | Thompson et al. | 556/429 |
| 2002/0195342 A1 | 12/2002 | Lee et al. | |
| 2006/0088844 A1 | 4/2006 | Xu | |

FOREIGN PATENT DOCUMENTS

| | | |
|---|---|---|
| WO | WO-03/037514 A2 | 5/2003 |
| WO | WO-2008080254 | 7/2008 |
| WO | WO-2008/101043 A1 | 8/2008 |
| WO | WO-2008092291 | 8/2008 |
| WO | WO-2009/059447 A1 | 5/2009 |
| WO | WO-2009/079856 A1 | 7/2009 |
| WO | WO-2009/079857 A1 | 7/2009 |

OTHER PUBLICATIONS

"European Application Serial No. 09173857.5, European Search Report mailed Mar. 25, 2010", 7 pgs.
Balss, K. M., et al., "DNA Hybridization Assays Using Temperature Gradient Focusing and Peptide Nucleic Acids", *J Am Chem Soc.*, 126(41), (Oct. 20, 2004), 13474-13479.
Crews, N., et al., "Continuous-flow thermal gradient PCR", *Biomedical Microdevices*, 10(2), (Apr. 2008), 187-195.
Crews, N., et al., "Product differentiation during continuous-flow thermal gradient PCR", *Lab Chip.*, 8(6), (Jun. 2008), 919-924.
Erickson, D., et al., "Electrokinetically based approach for single-nucleotide polymorphism discrimination using a microfluidic device", *Anal Chem.*, 77(13), (Jul. 1, 2005), 4000-4007.
Grover, J., et al., "Fast PCR Thermal Cycling Device", *IEEE Sensors Journal*, 8(5), (2008), 476-487.
Kajiyama, T., et al., "Genotyping on a thermal gradient DNA chip", *Genome Res.*, 13(3), (Mar. 2003), 467-475.
Mao, H., et al., "Reusable platforms for high-throughput on-chip temperature gradient assays", *Anal Chem.*, 74(19), (Oct. 1, 2002), 5071-5075.
Sundberg, S. O, et al., "Solution-phase DNA mutation scanning and SNP genotyping by nanoliter melting analysis", *Biomedical Microdevices*, 9(2), (Apr. 2007), 159-166.
Zhang, C., et al., "PCR microfluidic devices for DNA amplification", *Biotechnol Adv.*, 24(3), (May-Jun. 2006), 243-284.
Zhang, H. D., et al., "DNA mutation detection with chip-based temperature gradient capillary electrophoresis using a slantwise radiative heating system", *Lab on a Chip*, 7, (2007), 1162-1170.
"European Application Serial No. 09173857.5, Office Action mailed Apr. 8, 2010", 8 Pgs.
"European Application Serial No: 09173857.5, Response filed Aug. 17, 2010 to Communication dated Apr. 8, 2010", 14 pgs.
Zuker, Michael , "Online Computation Server Mfold", http://mfold.bioinfo.rpi.edu/cgi-bin/rna-form1.cgi, Rensselaer Polytechnic Institute, 2008.

* cited by examiner

*Primary Examiner* — James Martinell
(74) *Attorney, Agent, or Firm* — Schwegman, Lundberg & Woessner, P.A.

(57) ABSTRACT

A method and apparatus for real-time, simultaneous, qualitative measurement of one or more single nucleotide polymorphisms in one or more target nucleic acids is provided. This method involves combining a polymerase chain reaction (PCR) technique with an evanescent wave technique.

11 Claims, 1 Drawing Sheet

METHOD FOR SINGLE NUCLEOTIDE POLYMORPHISM AND MUTATION DETECTION USING REAL TIME POLYMERASE CHAIN REACTION MICROARRAY

BACKGROUND OF THE INVENTION

The most common type of genetic variation is single nucleotide polymorphism (SNP), which may include polymorphism in both DNA and RNA a position at which two or more alternative bases occur at appreciable frequency in the people population (>1%). Base variations with the frequency<1% are called point mutations. For example, two DNA fragments in the same gene of two individuals may contain a difference (e.g., AAGTACCTA to AAGTGCCTA) in a single nucleotide to form a single nucleotide polymorphism (SNP). Typically, there exist many single nucleotide polymorphism (SNP) positions (about $1/1000^{th}$ chance in whole genome) in a creature's genome. As a result, single nucleotide polymorphism (SNP) and point mutations represent the largest source of diversity in the genome of organisms, for example, a human.

Most single nucleotide polymorphisms (SNP) and point mutations are not responsible for a disease state. Instead, they serve as biological markers for locating a disease on the human genome map because they are usually located near a gene associated with a certain disease. However, many mutations have been directly linked to human disease and genetic disorder including, for example, Factor V Leiden mutations, hereditary haemochromatosis gene mutations, cystic fibrosis mutations, Tay-Sachs disease mutations, and human chemokine receptor mutations. As a result, detection of single nucleotide polymorphisms (SNPs) and similar mutations are of great importance to clinical activities, human health, and control of genetic disease.

Neutral variations are important, for example, because they can provide guideposts in the preparation of detailed maps of the human genome, patient targeted drug prescription, and identify genes responsible for complex disorder. Moreover, since genetic mutation of other species (e.g., bacteria, viruses, etc.) can also be regarded as a type of single nucleotide polymorphism (SNP), the detection of single nucleotide polymorphism (SNP) can also be used to diagnosis the drug resistance, phenotype/genotype, variants and other information of microorganisms that may be useful in clinical, biological, industrial, and other applications.

There are several methods for detecting single nucleotide polymorphism (SNP) and mutations. However, most of the methods are not suitable to be adapted to the platform of automated high-throughput assays or to multiplex screening.

BRIEF DESCRIPTION OF THE DRAWINGS

Embodiments of the invention may be best understood by referring to the following description and accompanying drawings, which illustrate such embodiments. In the drawings.

DETAILED DESCRIPTION OF THE INVENTION

Figure 1:
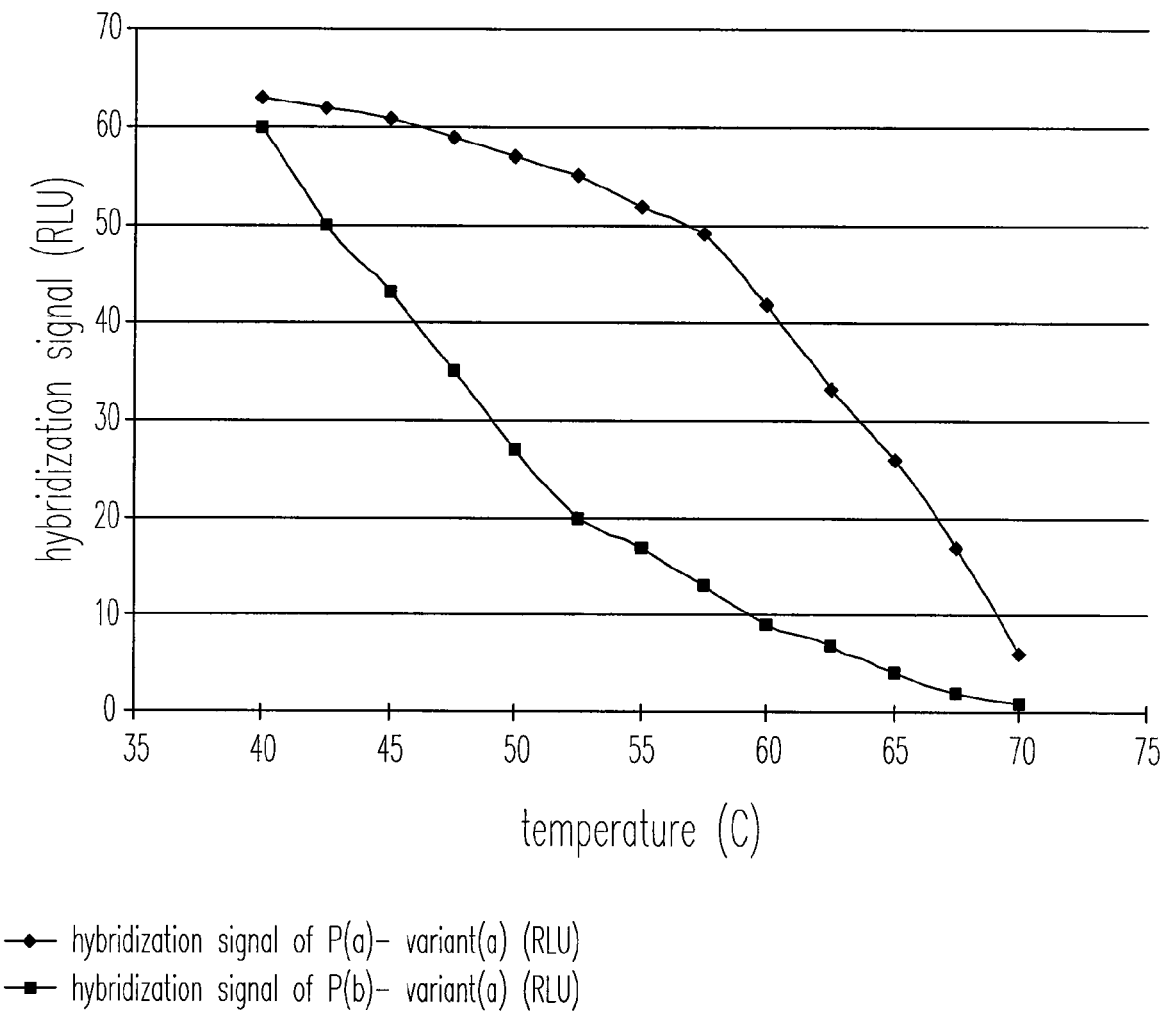
FIG. 1 illustrates a plot of the melting curves of Variant A of *E. aerogenes* with two probes P(a) and a P(b).

The present invention provides a method and an apparatus for determining the highly sensitive multiplex single nucleotide polymorphism and mutation detection using a real time polymerase chain reaction microarray. This method has many advantages including, for example, ease of operation in which all of the steps are integrated on one chip, multiplex single nucleotide polymorphism (SNP) detection in one chip, rapid analysis in less than 3 hours after extracting the DNA, high sensitivity due to amplification and fluorescence detection, labor saving due to automation, a more accurate hybridization signal is obtained when the measurement is performed over a wide temperature range, and poses very little biosafety hazard because all of reactions are carried out on one disposable chip.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *Hawley's Condensed Chemical Dictionary*, $14^{th}$ edition, Wiley Europe, 2002.

As used herein, the term "about" refers to a variation of 10 percent of the value specified.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the term "amplicon" refers to the product of a polymerase chain reactions (PCR). Amplicons are pieces of DNA that have been synthesized using amplification techniques (e.g., using a double-stranded DNA and two primers). The amplicon may contain, for example, a primer tagged with a fluorescent molecule at the 5' end.

As used herein, the term "buffer solution" refers to a solution that resists changes in the pH. A suitable reaction buffer for a microarray is described in PCT Patent Application Publication No. WO 2008/080254.

As used herein, the term "charge-coupled device" refers to a device for forming images electronically, using a layer of silicon that releases electrons when struck by incoming light.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Alternatively, there may be "complete" or "total" complementarity between the nucleic acids. The degree of complementarity between nucleic acid strands has significant effects on the efficiency and strength of hybridization between nucleic acid strands.

As used herein, the term "evanescent" refers to a nearfield standing wave exhibiting exponential decay with distance. As used in optics, evanescent waves are formed when sinusoidal waves are internally reflected off an interface at an angle greater than the critical angle so that total internal reflection occurs. A suitable evanescent wave system that may be used in the practice of this invention is described, for example, in U.S. Patent Application Publication No. 2006/0088844. A suitable microarray reader based on evanescent wave is described in PCT Patent Application Publication No. WO 2008/092291.

As used herein, the term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the melting temperature ($T_m$) of the formed hybrid, and the G:C ratio within the nucleic acids. A single molecule that contains pairing of complementary nucleic acids within its structure is said to be "self-hybridized."

As used herein, the term "light" refers to an electromagnetic radiation in the wavelength range including infrared, visible, ultraviolet, and X-rays.

As used herein, the term "linker" refers to a carbon chain, which may include other elements that covalently attach two chemical groups together.

As used herein, the term "microarray" is a linear or two-dimensional microarray of discrete regions, each having a defined area, formed on the surface of a solid support. An oligonucleotide probe microarray complementary to the target nucleic acid sequence or subsequence thereof is immobilized on a solid support using one of the display strategies described below. The methods described herein employ oligonucleotide microarrays which comprise target nucleic acid probes exhibiting complementarity to one or more target nucleic acid sequences. Typically, these target nucleic acid probes are DNA and are immobilized in a high-density microarray (i.e., a "DNA chip") on a solid surface.

As used herein, the term "nucleic acid" refers to any nucleic acid containing molecule including, but not limited to, DNA or RNA.

As used herein, the term "nucleic acid sequence" refers to an oligonucleotide, nucleotide or polynucleotide, and fragments or portions thereof, and to DNA or RNA of genomic or synthetic origin which may be single or double stranded, and represent the sense or antisense strand.

As used herein, the terms "nucleoside" and "nucleotide" refer to those moieties which contain not only the known purine and pyrimidine bases, but also other heterocyclic bases that have been modified.

As used herein, the term "optical detection path" refers to a configuration or arrangement of detection means to form a path whereby electromagnetic radiation is able to travel from an external source to a means for receiving radiation, wherein the radiation traverses the reaction chamber.

As used herein, the term "polymerase chain reaction (PCR)" refers to the method of K. B. Mullis, U.S. Pat. Nos. 4,683,195, 4,683,202, and 4,965,188. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double-stranded target sequence. To effect amplification, the mixture is denatured and the primers annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing, and extension constitute one "cycle" and there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the term "reactor" refers to a device, which can be used in any number of chemical processes involving a fluid.

As used herein, the term "single nucleotide polymorphism (SNP)" refers to a DNA sequence variation occurring when a single nucleotide—A, T, C, or G —in the genome (or other shared sequence) differs between members of a species (or between paired chromosomes in an individual).

As used herein, the term "substrate" refers to material capable of supporting associated assay components (e.g., assay regions, cells, test compounds, etc.).

As used herein, the term "target nucleic acid" refers to a polynucleotide, which includes at least two nucleotides. The polynucleotide is genetic material including, for example, DNA/RNA, mitochondrial DNA, rRNA, tRNA, mRNA, viral RNA, bacterial DNA or RNA, plasmid DNA, and eukaryote or prokaryote DNA or RNA.

As used herein, the term "melting temperature ($T_m$)" refers to the temperature at which a population of double-stranded nucleic acid molecules becomes half dissociated into single strands.

As used herein, the term "variant" refers to one kind of genotype or polynucleotide including a single nucleotide polymorphism (SNP) or point mutation site.

As used herein, the phrase "matched variant" refers to one kind of genotype or polynucleotide, which is complementary to the probe.

The present invention provides a qualitative method for determining one or more single nucleotide polymorphisms in one or more target nucleic acids. This method includes: (a) independently hybridizing over a temperature gradient one or more fluorescently tagged target amplicons to two or more target nucleic acid probes immobilized in independent areas on an upper surface of a substrate, wherein the sequences of the two or more target nucleic acid probes differ so as to represent one or more single nucleotide polymorphisms; (b) independently activating a fluorescence response from each of the one or more fluorescently tagged target amplicons hybridized to the two or more target nucleic acid probes immobilized in independent areas on the upper surface of the substrate using an evanescent wave of a predetermined wavelength; (c) independently detecting each fluorescence response; (d) independently analyzing each fluorescence response; (e) independently differentially hybridizing each of the one or more fluorescently tagged target amplicons hybridized to each of the two or more target nucleic acid probes to provide a melting curve for each of the one or more fluorescently tagged target amplicons hybridized to each of the two or more target nucleic acid probes; and (f) independently analyzing each melting curve, the $T_m$ of each melting curve, or the ratio of the fluorescence of the two or more target nucleic acid probes at a selected temperature to qualitatively determine whether the one or more target nucleic acid sequence has one or more single nucleotide polymorphisms, wherein the analyzing each melting curve comprises a comparison of hybridization signal at a single temperature, a comparison of hybridization signal over a temperature range, or a detection of a melting temperature ($T_m$) change using a melting curve.

In one embodiment, the method further includes amplifying the one or more target nucleic acids, wherein each of the one or more target nucleic acids has at least two different nucleotides at one single nucleotide polymorphism (SNP) site. In one embodiment, the amplifying occurs during a polymerase chain reaction. In another embodiment, the amplifying includes: (i) independently denaturing one or more target nucleic acids to provide one or more pairs of single-stranded target nucleic acids; (ii) independently annealing one or more primers to one or more pairs of single-stranded target nucleic acids; and (iii) independently extending each primer annealed to each single-stranded target nucleic acid to provide one or more fluorescently tagged target amplicons.

In one embodiment, the each of the two or more target nucleic acid probes includes a first subgroup and a second subgroup, wherein the first subgroup and the second subgroup each independently comprise one or more probes, wherein the nucleic acid sequence of each subgroup is complementary to the sequence of a corresponding matched variant, and further wherein each probes has two melting curves, one for the corresponding matched Variant and the other for another single base mismatched variant.

In one embodiment, the substrate includes silicon, glass, quartz, a ceramic, a rubber, a metal, a polymer, a hybridization membrane, or a combination thereof. In another embodiment, the substrate is chemically modified with a reagent selected from a silane, avidin, poly-L-lysine, streptavidin, a polysaccharide, a mercaptan, or a combination thereof. In yet another embodiment, the two or more target nucleic acid probes are printed and immobilized onto the substrate using a micro-array printer.

In one embodiment, the two or more target nucleic acid probes comprise a linker with a sulfhydryl (RSH), amino ($NH_2$), hydroxyl (OH), carboxaldehyde (CHO), or carboxylic acid (COOH) group at the 3' end. In another embodiment, the linker includes about a ten nucleotide random oligomer. In yet another embodiment, the two or more target nucleic acid probes are immobilized onto a silanized glass substrate with the sulfhydryl (RSH) group at the 3' end.

The present invention provides an apparatus. The apparatus includes: a closed reactor including: a substrate having opposing first and second planar opposing surfaces, the substrate having a cavity and a refractive index greater than a refractive index of water; a buffer layer arranged over the first planar surface of the substrate; a cover plate arranged over the buffer layer and the cavity, the cover plate in combination with the cavity and buffer layer defining a reaction chamber; and at least one inlet port and at least one outlet port to communicate with the reaction chamber through the substrate to enable the passage of fluid from an external source into and through the reaction chamber; a temperature control system coupled to the closed reactor to cycle the temperature of a buffer solution contained within the closed reactor to enable a plurality of polymerase chain reactions, wherein the buffer solution is substantially in contact with the first surface of the substrate and being capable of sustaining a plurality of polymerase chain reactions, a plurality of hybridization reactions, and containing one or more fluorescently tagged primers, one or more optionally fluorescently tagged dNTPs, and one or more target nucleic acids; a light source coupled to the closed reactor to provide a ray of light having a wavelength chosen to activate one or more fluorescently tagged target amplicons hybridized to two or more target nucleic acid probes immobilized in independent areas on the first surface of the substrate, incident on an interface between the substrate and the buffer solution at an angle chosen to propagate an evanescent wave into the buffer solution; and a detector coupled to the closed reactor to detect the one or more fluorescent responses emitted by one of the one or more fluorescently tagged target amplicons hybridized to two or more target nucleic acid probes immobilized in independent areas on the first surface of the substrate.

In one embodiment, the apparatus further includes an analyzer coupled to the detector to analyze the one or more fluorescence responses from the one or more fluorescently tagged target amplicons hybridized to the two or more target nucleic acid probes in independent areas on the first surface of the substrate and to analyze each melting curve of each of the one or more fluorescently tagged target amplicons hybridized to each of the two or more target nucleic acid probes to qualitatively determine the number of one or more single nucleotide polymorphisms in the one or more target nucleic acids.

In one embodiment, the detector is mobile and capable of sequentially detecting fluorescent light emitted by the one or more fluorescently tagged target amplicons attached to the one or more anti-recognition tag primer probes. In another embodiment, the closed reactor is mobile and capable of being sequentially addressed by the detector. In yet another embodiment, the detector includes a camera, a charge-coupled device, a charge-injection device, a complementary metal-oxide-semiconductor device, a video camera, a silicon photo-cell, a photodiode, an avalanche photodiode, a photo-multiplier tube, or a combination thereof.

An example of a polymerase chain reaction (PCR) microarray for the detection of a point mutation is given below. The target sequence for the species/variant identification is selected from its 16S rDNA, which could be amplified together with other species of bacteria by polymerase chain reaction (PCR) using a universal primer set. The universal primer set may include:

Upper Primer

5'-Cy5actcctacgggaggcagcag-3'        (SEQ ID NO: 1)

Lower Primer

5'-Cy5attaccgcggctgctggcac-3'        (SEQ ID NO: 2)

wherein Cy5 is a Cyanine 5 fluorescence tag. The primer set may be found via primer analysis using the Oligo 6 software (Molecular Biology Insights, Inc., Cascade, Colo., USA) in a group of 16S rDNA sequences from different species of bacteria. The primer sequence may be designed within the most conservative region of different bacteria species. The melting temperature ($T_m$) should be around 60° C.

Two variants of *E. aerogenes* are obtained from pure cultures of clinical samples, which have already been identified using conventional biochemical methodologies. The 16S rDNA of these two variants of *E. aerogenes* is purified and sequenced using the universal primer set without cy5 conjugation. The sequencing results are as followed:

Variant A:
5'CaaGCCTGATGCAGCCATGCCGCGTGTAT        (SEQ ID NO: 3)

GAAGAAGGCCTTCGGGTTGTAAAGTACTTTC

***AGCGAGGAGGAAGGCG*TTAA**GGTTAATAACC

TTGGCGATTGACGTTACTCGCAGAAGAAGCA

CCGGCTAACTCCGTGCCAGCAGCCGCGG-TAA

TA 3'

Variant B:
5'caAGCCTGATGCAGCCATGCCGCGTGTAT (SEQ ID NO: 4)

GAAGAAGGCCTTCGGGTTGTAAAGTACTTTC

*AGCGAGGAGGAAGGCATTAA*GGTTATTAAAC

CTTGGCGATTGACGTTACTCGCAGAAGAAGC

ACCGGCTAACTCCGTGCCAGCAGCCGCGGTA

ATA 3'

Within the bold area, only one single base difference exists: AAGGCGTTAA (SEQ ID NO:5) in Variant A versus AAGGCATTAA (SEQ ID NO:6) in Variant B. The base G (guanine) in Variant A is replaced by base A (adenine) in Variant B. To discriminate this difference, Probe A (i.e., P(a)) and Probe B (i.e., P(b)) should be designed to be complementary to Variant A and Variant B, respectively, as shown below:

The Sequence of Probe A

5'-AGCGAGGAGGAAGGC (SEQ ID NO: 7)
GTTAAGGTTAA-3'

The Sequence of Probe B

5'-AGCGAGGAGGAAGGC (SEQ ID NO: 8)
ATTAAGGTTAA-3'

These probes may be designed using software such as Array Designer 4 (Premier Biosoft International, Palo Alto, Calif., USA), which can screen probes for their sequence features, thermodynamic properties and secondary structures.

In one embodiment, the length of probes should be about 15 to 35 nucleotides. Typically, these probes should be short oligonucleotides less than 20 nucleotides with 30-50% G+C content, designed with the discriminating nucleotide located near the middle of the probe. Longer probes may be used to compensate for regions that have low G+C content. G:T and G:A mismatches may be slightly destabilizing, whereas the effect may be greater for A:A, T:T, C:T, and C:A mismatches. Therefore, the choice of the sense or anti-sense strand may affect specificity. (e.g., a C:A mismatch is often easier to discriminate than a G:T mismatch). The choice of probe sequences can involve a considerable amount of trial-and-error testing of candidate probes. Candidate probes should be evaluated individually using known positive and negative control samples. In another embodiment, the melting temperature ($T_m$) of hybridizations should be similar to the annealing temperature of the polymerase chain reaction (PCR). In yet another embodiment, the sequences have two or more unique bases to distinguish with probes specific to other species.

In one embodiment, Probe A and Probe B may be synthesized with an amino (e.g., —$NH_2$) group at 5' end. To reduce potential space hindrance, a linker made of a 10 nucleotide random oligomer may be added at 5' end. Correspondingly, a —$NH_2$ group may be modified at 5' end of the linker. The folding conformations of the probes with linkers can be calculated, for example, by the online computation server Mfold (see, e.g., /mfold.bioinfo.rpi.edu/cgi-bin/rna-form1.cgi). The results with high $^\Delta G$ are not used.

These two probes are immobilized onto a modified silane glass with NH2-group, together with other probes specific to other species of bacteria. These probes can be spotted with an aspirate-dispensing arrayer, like Biodot Arrayer (Cartesian Technologies, Irvine, Calif., USA) or similar contact-spotting arrayers. The probes can be arranged in the format of an array on the surface of the silane glass.

The glass with immobilized probes array may be assembled with a plastic piece to form a reaction chamber, inside which the polymerase chain reaction (PCR) reaction and the hybridization reaction may be carried out simultaneously.

A small copy number of purified genomic DNA from Variant A can act as the template of the polymerase chain reaction (PCR). These templates are added into the reaction chamber together with deoxynucleotide triphosphates (dNTPs, for example, the nucleotides adenine (A), thymine (T), cytosine (C) and guanine (G)), a cy5 labeled primer set, Taq polymerase, and a proper buffer for the amplification and the hybridization reaction. The chamber may be sealed with a set of rubber plugs before the amplification reaction.

The chamber may be heated and cooled with a semi-conductor cooler to following the temperature of polymerase chain reaction (PCR) cycles. During each annealing step of a polymerase chain reaction (PCR), the amplicons are hybridized with specific probes immobilized in the glass substrate. The hybridization between fluorescently labeled amplicons and probes is detected by evanescent wave during annealing steps of polymerase chain reaction (PCR). A suitable evanescent wave system that may be used in the practice of this invention is described, for example, in U.S. Patent Application Publication No. 2006/0088844.

After the polymerase chain reaction (PCR) is completed, the target fragments of Variant A are amplified to sufficient quantities to perform the melting curve detection. A program for detecting a hybridization signal with a continuously increasing temperature gradient may be set up, for example, from 35° C. to 85° C. at a temperature increment of 2° C./min.

At the same time during the range of different hybridization temperatures, for example, at every two centigrade, such as 35° C., 37° C., 39° C., 41° C. . . . 81° C., 83° C., 85° C., the hybridization signal between Probe A or B and Variant A may be recorded by evanescent wave detection. Thus, Variant A may provide two melting curves from 85° C. to 35° C. These two melting curves may distinguish the hybridization properties of the Probe A-Variant A duplex and Probe B-Variant A duplex. In a similar fashion, two melting curves may distinguish the hybridization properties of Probe A-Variant B duplex and Probe B-Variant B duplex.

The variant of *E. aerogenes* in the sample test can be easily discriminated by comparing the melting curves, as Variant A may show a melting curve of Probe A-Variant A with a higher signal than Probe B-Variant A (see, e.g., FIG. 1), while Variant B show a melting curve of Probe B-Variant B with a higher signal than Probe A-Variant B.

Another method may use the melting temperature ($T_m$) difference of each curve to analyze each variant. If a mismatch exists between the probe and the variant, the melting temperature decreases. As used herein, the melting temperature ($T_m$) represents the temperature at which the hybridization signal is reduced to 50% of the saturated hybridization signal. For example, if the melting temperature ($T_m$) of Probe A target nucleic acid equals that of Probe A-Variant A, this may indicate the presence of Variant A. If the melting temperature ($T_m$) of Probe A target nucleic acid equals that of Probe A-Variant B (less than that of Probe A-Variant A), this may indicate the presence of Variant B.

Another method may use the hybridization signal ratio of Probe A and Probe B at an appointed temperature. For example, the hybridization signal ratio of Probe A-target variant: Probe B-target variant at 50° C. A ratio larger than 3 may indicate the presence of Variant A, while a ratio less than 0.3 may indicate the presence of Variant B. A ratio in the range of 0.5-2 may indicate the coexistence of Variant A and B in the sample.

One example for the parallel identification of four globin gene point mutations related to α-Thalassemia is:

```
(1)    α2 initiation codon     CCATGG > CCACGG (2)    α1 initiation codon     CCATGG > CCGTGG (3)    α2 Cd 142 C             CGTTAA > CGTCAA (4)    α2 Cd 142 A             CGTTAA > CGTAAA
```

These four point mutations are located at two genes: α1-globin gene and α2-globin gene. Three primers are designed to co-amplify these two genes.

```
Primer C (5' α common):             (SEQ ID NO: 9)
5'-cy5-CCAAGCATAAACCCTGGCGCGCT-3'

Primer 1 (3' α1 gene):              (SEQ ID NO: 10)
5'-cy5-CCATGCTGGCACGTTTCTGAG-3'

Primer 2 (3' α2 gene):              (SEQ ID NO: 11)
5'-cy5-AACACCTCCATTGTTGGCACATTCC-3'
```

Primer C and Primer 1 are used for the amplification of α1 gene and Primer C and Primer 2 is used for the amplification of α2 gene. The sequence length of fluorescently tagged target amplicons is 923 base pairs (bp) for α2 and 922 base pairs (bp) for globin α1 gene.

Eight oligonucleotide probes are designed for the point mutation sites as described below. There are two probes for every point mutation site. The normal probe matches the normal target molecule, while the variant probe matches the variant target molecule.

DNA samples purified from blood leukocytes were added into the reaction chamber and amplified with polymerase chain reactions (PCR). After the polymerase chain reactions (PCR), the hybridization signals of each probe with the fluorescently tagged amplicons were detected with evanescent wave. The results can be analyzed with following three alternative methods.

In the first method, the hybridization signal ratio of normal probe and variant probe at an appointed temperature is analyzed. A ratio larger than an appointed value A may indicate the presence of normal target sequence at this site. A ratio less than an appointed value B may indicate the presence of variant target sequence at this site. A ratio falling into a range C-D indicates the coexistence of normal and variant target sequence. For different mutation site, (e.g., four different mutation sites), the values of A, B, C, and D may be set differentially.

In the second method, the melting curves are analyzed. For each mutation site, two melting curves may be obtained with the method as described in the example described above. By comparing the two melting curves of each mutation site, the hybridization signals of normal probe and variant probe may be compared at a wide temperature range. This method may be more accurate than comparing the hybridization signals at one temperature, as described in the example above. For example, if the shape of the detected melting curve includes an inflexion point, then at this site, both the normal target molecule and the variant target molecules exist in the sample.

In the third method, the melting temperatures ($T_m$) are analyzed. As described above, the melting temperature ($T_m$) represents the temperature at which the hybridization signal will be reduced to 50% of the saturated hybridization signal. The melting temperature ($T_m$) value is determined by the sequence information of the probe and the ingredient of hybridization buffer. The melting temperature ($T_m$) may be calculated via analysis of melting curve. By this method, one probe for each mutation site may be used. For example, as described in the example above, four variant probes may be used for the detection of four mutation sites. The melting temperature ($T_m$) of each variant probe and its corresponding variant target molecules is a constant, for example, $T_m$ (1) for

|   | Mutation Site | | Sequence | |
|---|---|---|---|---|
| 1 | α2 initiation codon | Normal | 5' ACCCACCATGGTGCTGT 3' | (SEQ ID NO: 12) |
| 2 | | Variant | 5' CCCACCACGGTGCTGT 3' | (SEQ ID NO: 13) |
| 3 | α1 initiation codon | Normal | 5' ACCCACCATGGTGCTGT 3' | (SEQ ID NO: 14) |
| 4 | | Variant | 5' ACCCACCGTGGTGCTG 3' | (SEQ ID NO: 15) |
| 5 | α2 Cd 142 C | Normal | 5' AAATACCGTTAAGCTGGA 3' | (SEQ ID NO: 16) |
| 6 | | Variant | 5' AATACCGTCAAGCTGGA 3' | (SEQ ID NO: 17) |
| 7 | α2 Cd 142 A | Normal | 5' AAATACCGTTAAGCTGGA 3' | (SEQ ID NO: 18) |
| 8 | | Variant | 5' AAATACCGTAAAGCTGGA 3' | (SEQ ID NO: 19) |

The eight oligonucleotide probes with an amino (—NH$_2$) linker were immobilized in the activated glass surface in array format, and the glass was assembled into a reaction chamber for evanescent wave detection. A suitable evanescent wave system that may be used in the practice of this invention is described, for example, in U.S. Patent Application Publication No. 2006/0088844.

variant probe 1, $T_m$ (2) for variant probe 2, $T_m$ (3) for variant probe 3, and $T_m$ (4) for variant probe 4. If the variant target molecules of probe 1 are displaced by the normal target molecules in the hybridization reaction, sequence mismatch between the variant probe and the normal target molecules will cause a decrease of melting temperature ($T_m$). As a result, the sequence mismatch may cause the probe-target molecule complex to disassociate at a lower temperature because of the relatively low binding capacities between the probe and target molecules. For example, the variant probe 1-variant target molecule 1 complex will disassociate to 50% of the saturated hybridization signal at 65° C., while variant probe 1-normal target molecule 1 complex will disassociate to 50% of the saturated hybridization signal at 60° C.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

What is claimed is:

1. A qualitative method for determining one or more single nucleotide polymorphisms in one or more target nucleic acids comprising:
   (a) independently hybridizing over a temperature gradient one or more fluorescently tagged target amplicons to two or more target nucleic acid probes immobilized in independent areas on an upper surface of a substrate, wherein the sequences of the two or more target nucleic acid probes differ so as to represent one or more single nucleotide polymorphisms;
   (b) independently activating a fluorescence response from each of the one or more fluorescently tagged target amplicons hybridized to the two or more target nucleic acid probes immobilized in independent areas on the upper surface of the substrate using an evanescent wave of a predetermined wavelength;
   (c) independently detecting each fluorescence response;
   (d) independently analyzing each fluorescence response;
   (e) independently differentially hybridizing each of the one or more fluorescently tagged target amplicons hybridized to each of the two or more target nucleic acid probes to provide a melting curve for each of the one or more fluorescently tagged target amplicons hybridized to each of the two or more target nucleic acid probes; and
   (f) independently analyzing each melting curve, the $T_m$ of each melting curve, or the ratio of the fluorescence of the two or more target nucleic acid probes at a selected temperature to qualitatively determine whether the one or more target nucleic acid sequence has one or more single nucleotide polymorphisms, wherein the analyzing each melting curve comprises a comparison of hybridization signal at a single temperature, a comparison of hybridization signal over a temperature range, or a detection of a melting temperature ($T_m$) change using a melting curve.

2. The qualitative method of claim 1, further comprising amplifying the one or more target nucleic acids, wherein each of the one or more target nucleic acids has at least two different nucleotides at one single nucleotide polymorphism (SNP) site.

3. The qualitative method of claim 2, wherein the amplifying occurs during a polymerase chain reaction.

4. The qualitative method of claim 2, wherein the amplifying comprises:
   (i) independently denaturing one or more target nucleic acids to provide one or more pairs of single-stranded target nucleic acids;
   (ii) independently annealing one or more primers to one or more pairs of single-stranded target nucleic acids; and
   (iii) independently extending each primer annealed to each single-stranded target nucleic acid to provide one or more fluorescently tagged target amplicons.

5. The qualitative method of claim 1, wherein each of the two or more target nucleic acid probes comprises a first subgroup and a second subgroup, wherein the first subgroup and the second subgroup each independently comprise one or more probes, wherein the nucleic acid sequence of each subgroup is complementary to the sequence of a corresponding matched variant, and further wherein each probes has two melting curves, one for the corresponding matched variant and the other for another single base mismatched variant.

6. The qualitative method of claim 1, wherein the substrate comprises silicon, glass, quartz, a ceramic, a rubber, a metal, a polymer, a hybridization membrane, or a combination thereof.

7. The qualitative method of claim 1, wherein the substrate is chemically modified with a reagent selected from a silane, avidin, poly-L-lysine, streptavidin, a polysaccharide, a mercaptan, or a combination thereof.

8. The qualitative method of claim 1, wherein the two or more target nucleic acid probes are printed and immobilized onto the substrate using a micro-array printer.

9. The qualitative method of claim 8, wherein the two or more target nucleic acid probes comprise a linker with a sulfhydryl (RSH), amino ($NH_2$), hydroxyl (OH), carboxaldehyde (CHO), or carboxylic acid (COOH) group at the 3' end.

10. The qualitative method of claim 9, wherein the linker comprises about a ten nucleotide random oligomer.

11. The qualitative method of claim 8, wherein the two or more target nucleic acid probes are immobilized onto a silanized glass substrate with the sulfhydryl (RSH) group at the 3' end.

* * * * *

SEQUENCE LISTING

```
<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
actcctacgg gaggcagcag                                                    20

<210> SEQ ID NO 2
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 2
attaccgcgg ctgctggcac                                                    20

<210> SEQ ID NO 3
<211> LENGTH: 155
<212> TYPE: DNA
<213> ORGANISM: Enterobacter aerogenes

<400> SEQUENCE: 3
caagcctgat gcagccatgc cgcgtgtatg aagaaggcct tcgggttgta aagtactttc        60
agcgaggagg aaggcgttaa ggttaataac cttggcgatt gacgttactc gcagaagaag       120
caccggctaa ctccgtgcca gcagccgcgg taata                                  155

<210> SEQ ID NO 4
<211> LENGTH: 155
<212> TYPE: DNA
<213> ORGANISM: Enterobacter aerogenes

<400> SEQUENCE: 4
caagcctgat gcagccatgc cgcgtgtatg aagaaggcct tcgggttgta aagtactttc        60
agcgaggagg aaggcattaa ggttaataac cttggcgatt gacgttactc gcagaagaag       120
caccggctaa ctccgtgcca gcagccgcgg taata                                  155

<210> SEQ ID NO 5
```

```
<211> LENGTH: 10
<212> TYPE: DNA
<213> ORGANISM: Enterobacter aerogenes

<400> SEQUENCE: 5
aaggcgttaa                                                          10

<210> SEQ ID NO 6
<211> LENGTH: 10
<212> TYPE: DNA
<213> ORGANISM: Enterobacter aerogenes

<400> SEQUENCE: 6
aaggcattaa                                                          10

<210> SEQ ID NO 7
<211> LENGTH: 26
<212> TYPE: DNA
<213> ORGANISM: Enterobacter aerogenes

<400> SEQUENCE: 7
agcgaggagg aaggcgttaa ggttaa                                        26

<210> SEQ ID NO 8
<211> LENGTH: 26
<212> TYPE: DNA
<213> ORGANISM: Enterobacter aerogenes

<400> SEQUENCE: 8
agcgaggagg aaggcattaa ggttaa                                        26

<210> SEQ ID NO 9
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 9
ccaagcataa accctggcgc gct                                           23

<210> SEQ ID NO 10
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 10
ccatgctggc acgtttctga g                                             21

<210> SEQ ID NO 11
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 11
aacacctcca ttgttggcac attcc                                         25

<210> SEQ ID NO 12
<211> LENGTH: 17
<212> TYPE: DNA
<213> ORGANISM: Homo sapiens
```

```
<400> SEQUENCE: 12
acccaccatg gtgctgt                                                  17

<210> SEQ ID NO 13
<211> LENGTH: 16
<212> TYPE: DNA
<213> ORGANISM: Homo sapiens

<400> SEQUENCE: 13
cccaccacgg tgctgt                                                   16

<210> SEQ ID NO 14
<211> LENGTH: 17
<212> TYPE: DNA
<213> ORGANISM: Homo sapiens

<400> SEQUENCE: 14
acccaccatg gtgctgt                                                  17

<210> SEQ ID NO 15
<211> LENGTH: 16
<212> TYPE: DNA
<213> ORGANISM: Homo sapiens

<400> SEQUENCE: 15
acccaccgtg gtgctg                                                   16

<210> SEQ ID NO 16
<211> LENGTH: 18
<212> TYPE: DNA
<213> ORGANISM: Homo sapiens

<400> SEQUENCE: 16
aaataccgtt aagctgga                                                 18

<210> SEQ ID NO 17
<211> LENGTH: 17
<212> TYPE: DNA
<213> ORGANISM: Homo sapiens

<400> SEQUENCE: 17
aataccgtca agctgga                                                  17

<210> SEQ ID NO 18
<211> LENGTH: 18
<212> TYPE: DNA
<213> ORGANISM: Homo sapiens

<400> SEQUENCE: 18
aaataccgtt aagctgga                                                 18

<210> SEQ ID NO 19
<211> LENGTH: 18
<212> TYPE: DNA
<213> ORGANISM: Homo sapiens

<400> SEQUENCE: 19
aaataccgta aagctgga                                                 18
```